United States Patent [19]

Li

[11] Patent Number: 5,549,636

[45] Date of Patent: Aug. 27, 1996

[54] SURGICAL GRASPER WITH ARTICULATED FINGERS

[75] Inventor: Lehmann K. Li, Milford, Conn.

[73] Assignee: Li Medical Technologies Inc., Shelton, Conn.

[21] Appl. No.: 318,468

[22] Filed: Oct. 5, 1994

[51] Int. Cl.[6] ............................................. A61B 17/28
[52] U.S. Cl. ........................ 606/206; 606/205; 606/207; 623/64
[58] Field of Search ......................... 606/141, 205–210; 600/204, 216, 218; 604/272, 264, 239; 623/64; 128/751; 294/19.1, 19.2, 106

[56] References Cited

U.S. PATENT DOCUMENTS

| | | | |
|---|---|---|---|
| 632,843 | 9/1899 | McGhee | 606/207 X |
| 1,592,836 | 7/1926 | Moench. | |
| 2,659,896 | 11/1953 | Biasi | 623/64 |
| 3,074,408 | 1/1963 | Chester. | |
| 3,785,381 | 1/1974 | Lower et al.. | |
| 3,828,791 | 8/1974 | Santos. | |
| 3,888,117 | 6/1975 | Lewis. | |
| 4,066,082 | 1/1978 | Arcan et al.. | |
| 4,105,030 | 8/1978 | Kercso. | |
| 4,174,715 | 11/1979 | Hasson. | |
| 4,201,213 | 5/1980 | Townsend. | |
| 4,239,036 | 12/1980 | Krieger | 600/206 |
| 4,414,985 | 11/1983 | Myer. | |
| 4,466,649 | 8/1984 | Ozawa | 294/19 R |
| 4,607,620 | 8/1986 | Storz. | |
| 4,646,751 | 3/1987 | Maslanka | 128/751 |
| 4,722,338 | 2/1988 | Wright et al.. | |
| 4,733,663 | 3/1988 | Farley. | |
| 4,777,948 | 10/1988 | Wright. | |
| 4,792,333 | 12/1988 | Kidder | 604/83 |
| 4,944,741 | 7/1990 | Hasson | 606/206 |
| 4,994,079 | 2/1991 | Genese et al. | 606/206 |
| 5,014,407 | 5/1991 | Boughten et al.. | |
| 5,030,216 | 7/1991 | Theeuwes et al. | 604/892.1 |
| 5,047,046 | 9/1991 | Bodoia | 606/205 |
| 5,057,114 | 10/1991 | Wittich et al. | 606/127 |
| 5,064,428 | 11/1991 | Cope et al. | 606/127 |
| 5,070,859 | 12/1991 | Waldvogel. | |
| 5,089,000 | 2/1992 | Agee et al. | 606/170 |
| 5,108,406 | 4/1992 | Lee | 606/106 |
| 5,127,909 | 7/1992 | Shickman | 604/165 |
| 5,176,700 | 1/1993 | Brown et al. | 606/206 |
| 5,190,541 | 3/1993 | Abele et al. | 606/46 |
| 5,209,755 | 5/1993 | Abrahan et al. | 606/132 |
| 5,290,299 | 3/1994 | Fain et al. | 606/142 |
| 5,324,518 | 6/1994 | Orth et al. | 424/423 |
| 5,417,709 | 5/1995 | Slater | 606/205 |

FOREIGN PATENT DOCUMENTS 1049059 10/1983 U.S.S.R..

*Primary Examiner*—Michael H. Thaler
*Assistant Examiner*—Patrick W. Rasche
*Attorney, Agent, or Firm*—Ostrolenk, Faber, Gerb & Soffen, LLP

[57] ABSTRACT

Surgical apparatus including a support rod having proximal and distal ends; at least one articulated finger at the distal end of the support rod; a handle at the proximal end of the support rod, the handle having a finger grip adapted to be actuated by the hand of a user; a connecting member connecting the finger grip and the finger; a thumb being disposed at the distal end of the support rod opposite the finger, a spring biasing the finger toward a retracted position; and the finger being responsive to a tension in the connecting member exerted by movement of the finger grip whereby the finger moves in a defined manner toward the thumb for grasping an object. In a modified embodiment, a plurality of fingers are provided for opening up an internal space in a body or to grasp a body part to facilitate other surgical procedures.

73 Claims, 11 Drawing Sheets

FIG. 3
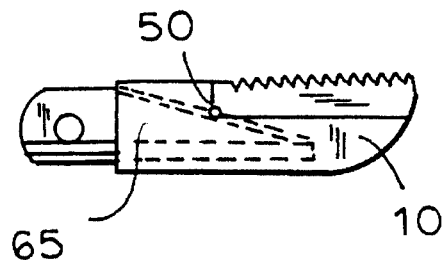
FIG. 5
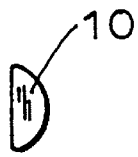
FIG. 6
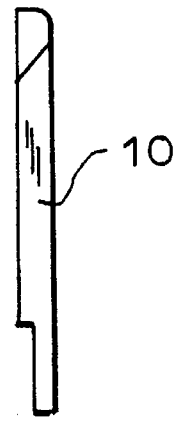
FIG. 4
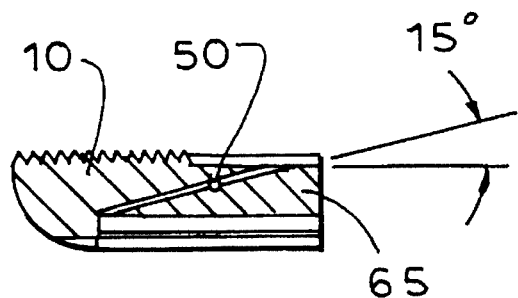
FIG. 3A

FIG. 7
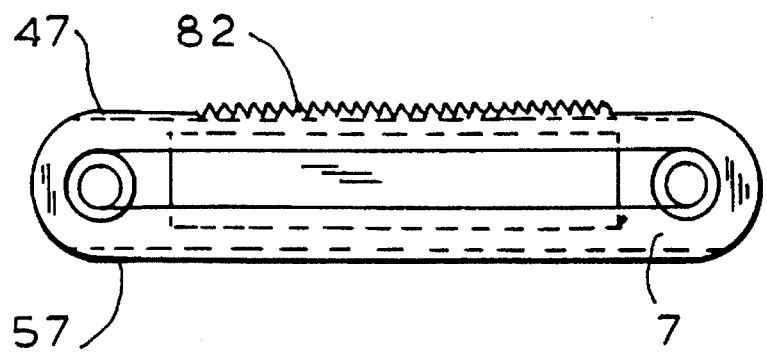
FIG. 8
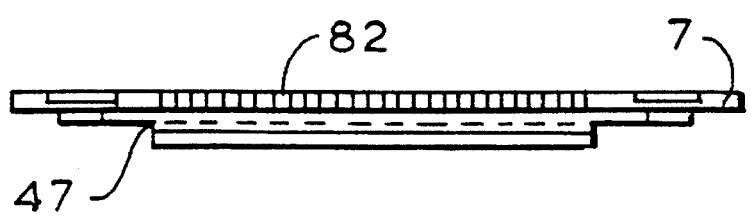
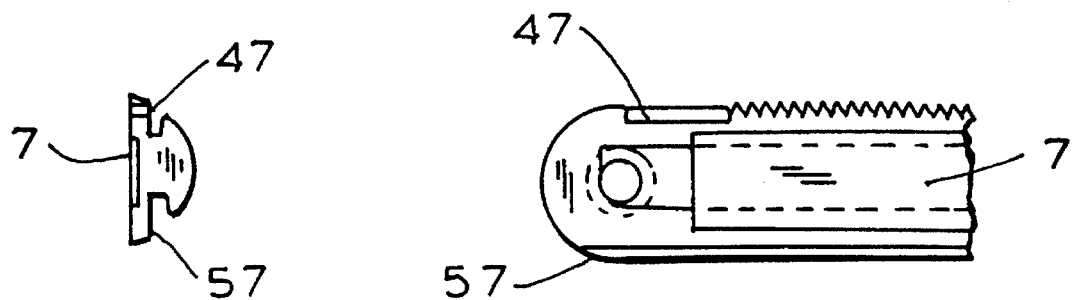
FIG. 10    FIG. 9

FIG. 11
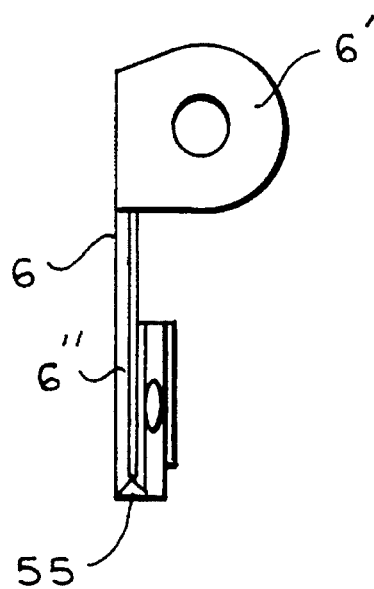
FIG. 14
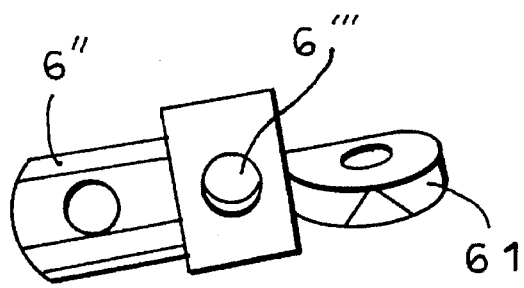
FIG. 12
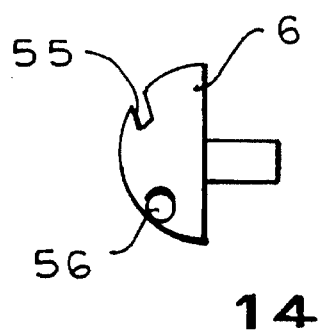
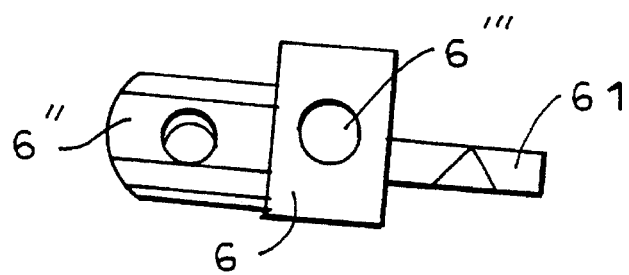
FIG. 13

FIG.15
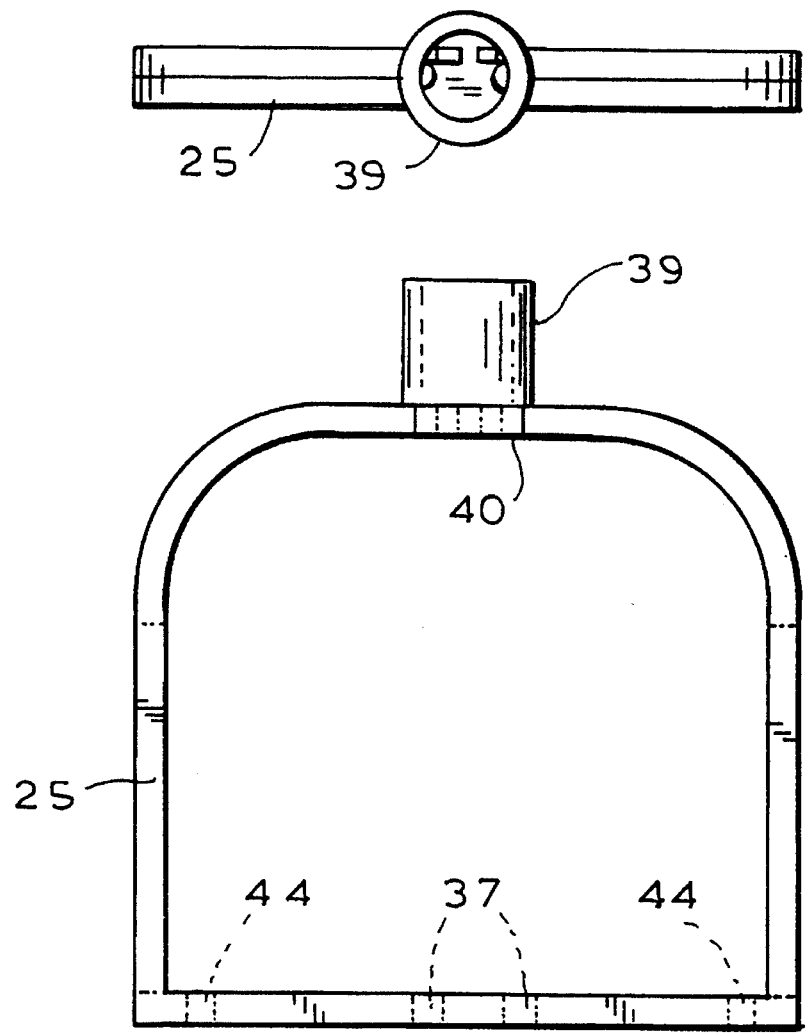
FIG.16
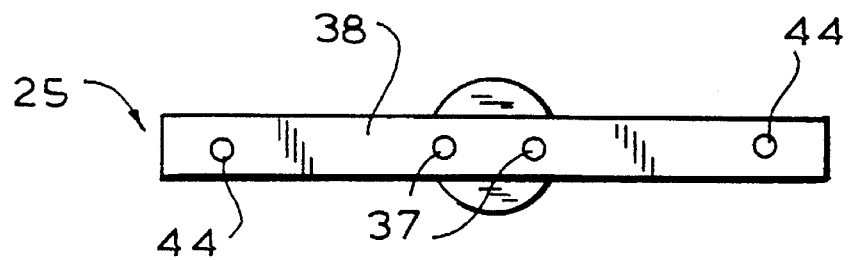
FIG.17

FIG. 20
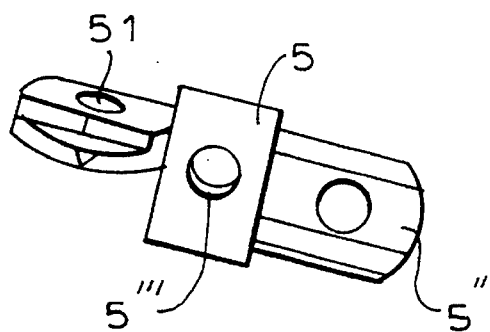
FIG. 18
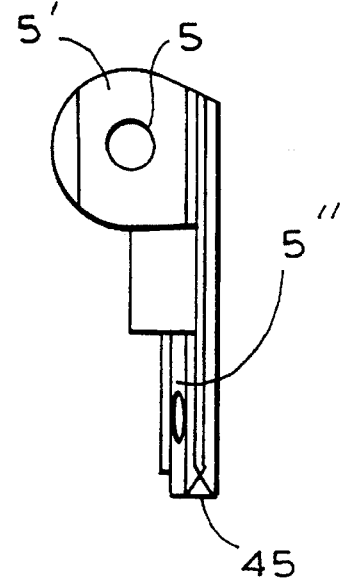
FIG. 21
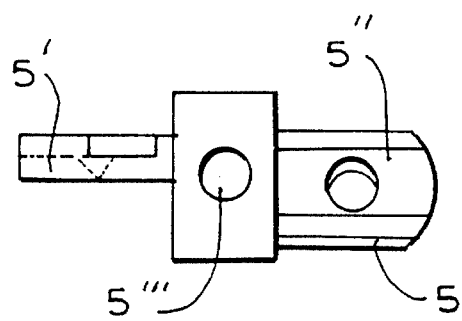
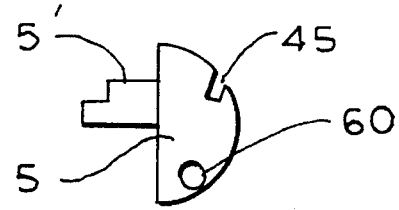
FIG. 19

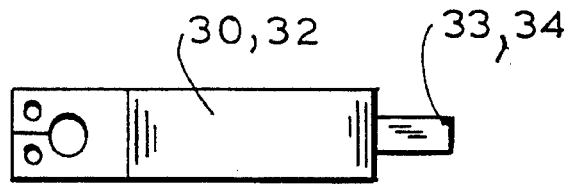
FIG. 22  FIG. 31
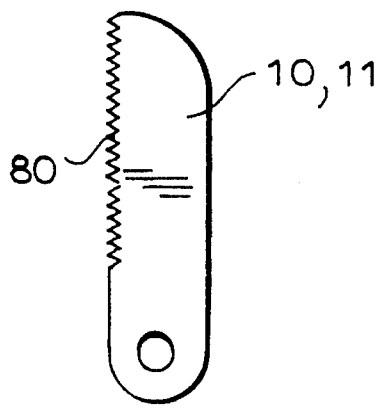
FIG. 30
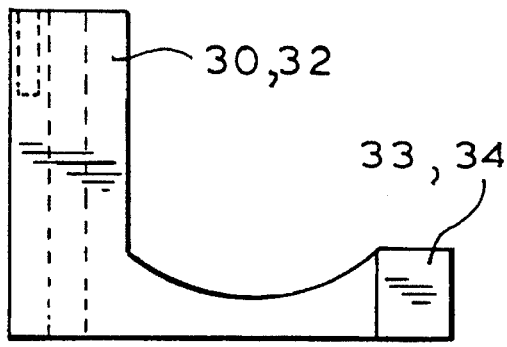
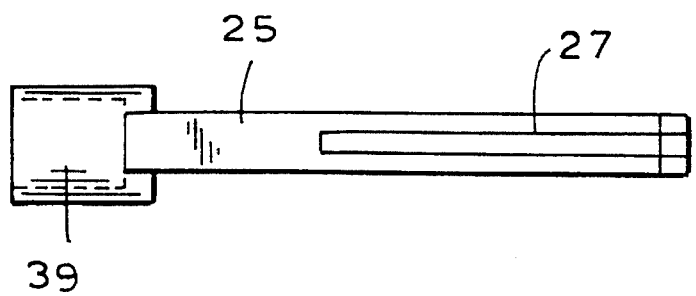
FIG. 23
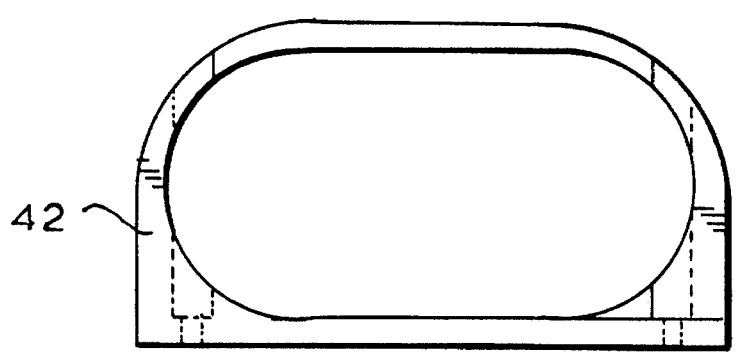
FIG. 29

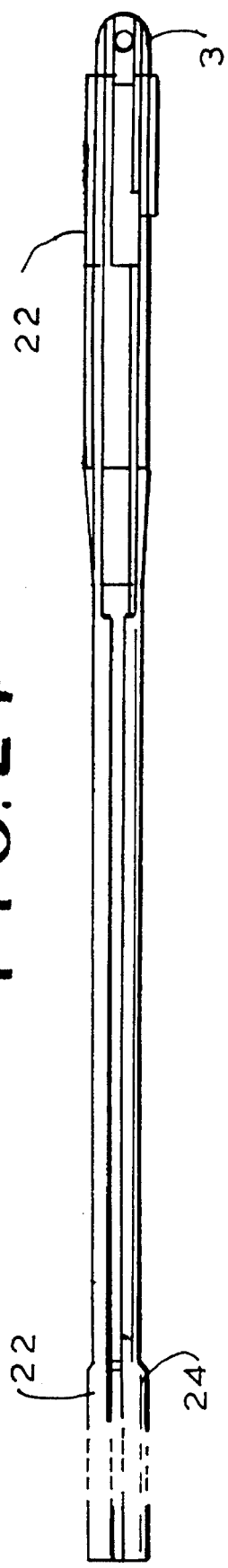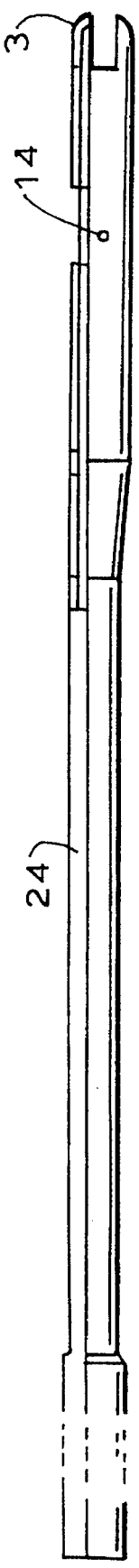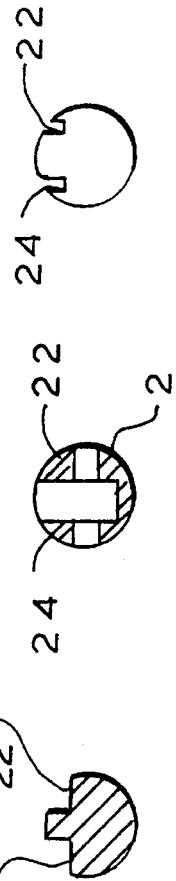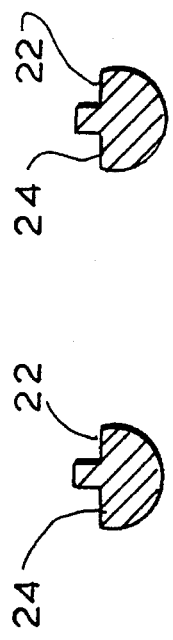
FIG. 24  FIG. 25  FIG. 26  FIG. 27  FIG. 28  FIG. 24A

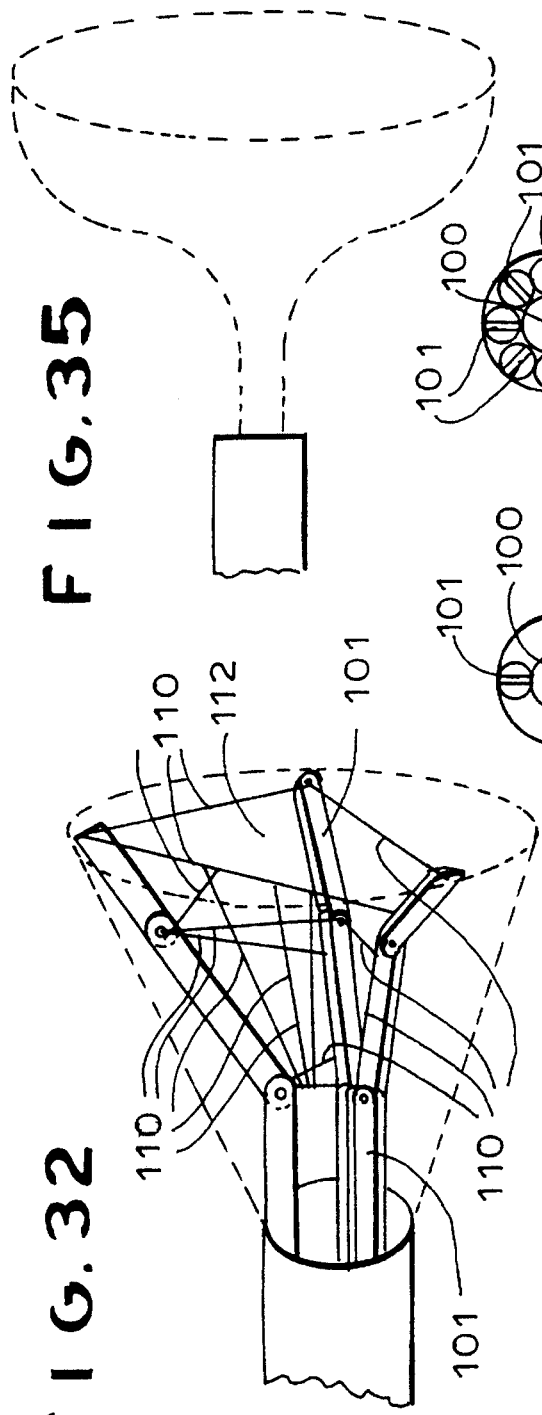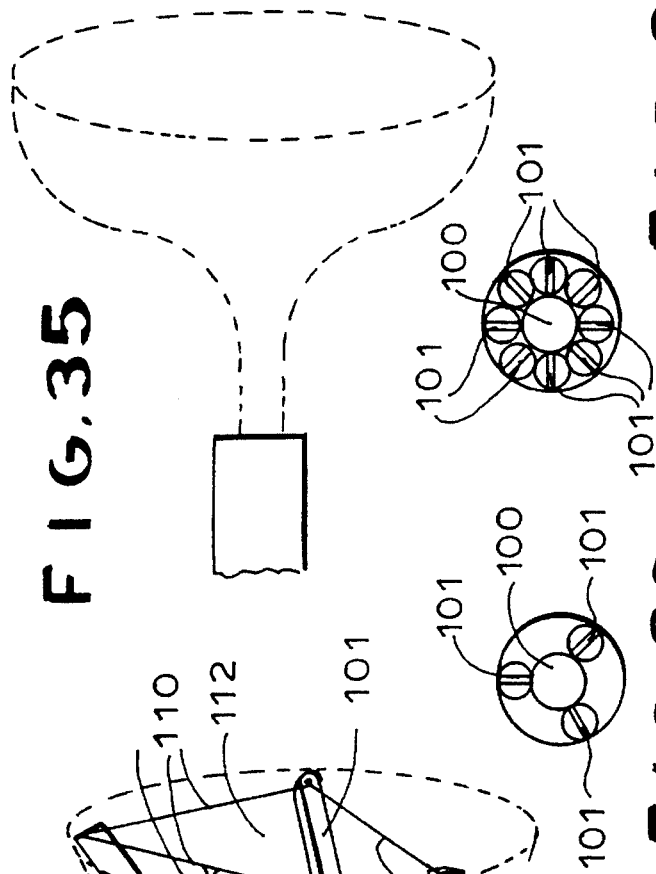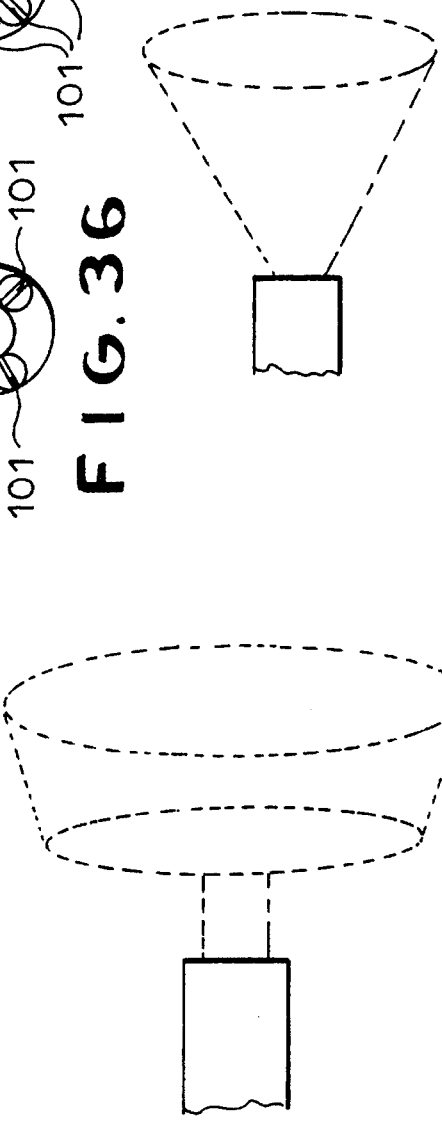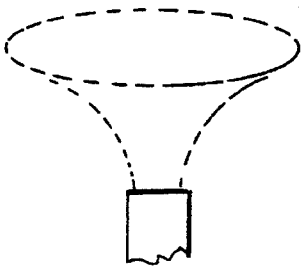

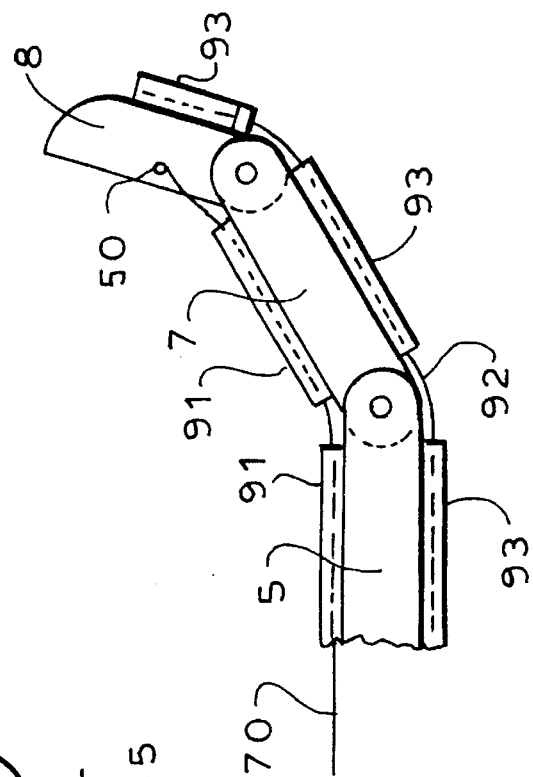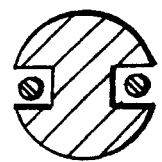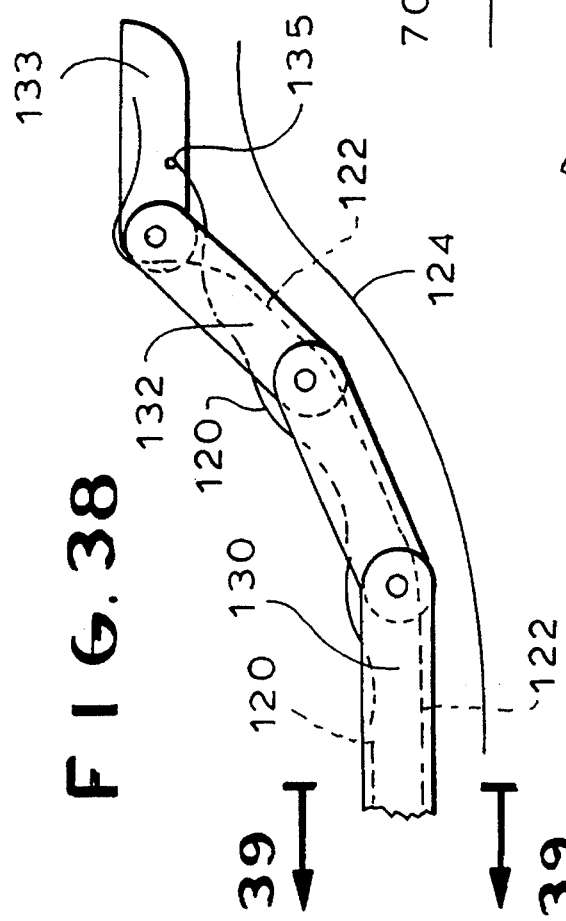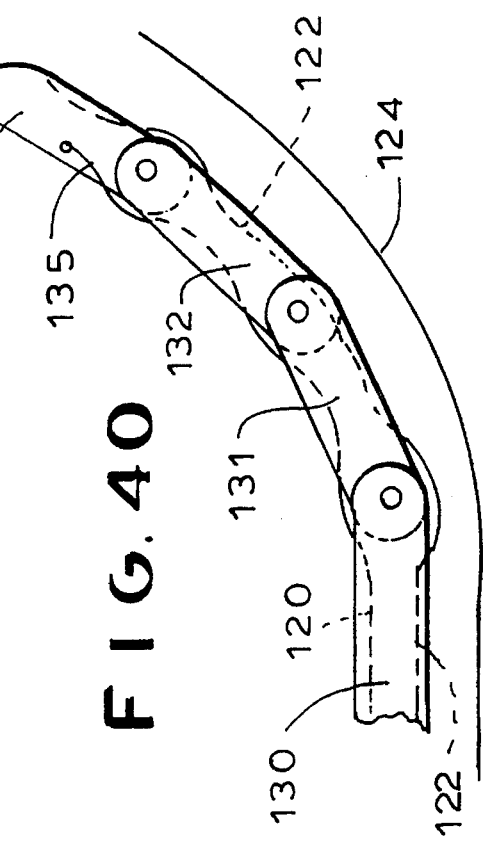

SURGICAL GRASPER WITH ARTICULATED FINGERS

BACKGROUND OF THE INVENTION

The present invention relates to medical devices, and in particular to a surgical device for operating within the confines of a human or animal body. The invention thus relates to internal surgical instruments, and in particular, relates to a surgical grasping or holding tool as well as a surgical tool for maintaining an opening within the body in which operations can be performed by other tools, for example, scalpels, scissors, cauterizers, lasers, fiber optical devices or drug delivery devices, etc. The invention allows the delivery of other functions and permits the displacement of internal body parts thereby to facilitate these other functions.

The following patents relating to surgical or other devices are known to applicant:

| | | |
|---|---|---|
| 1,592,836 | 4,607,620 | 5,057,114 |
| 3,074,408 | 4,722,338 | 5,064,428 |
| 3,785,381 | 4,733,663 | 5,070,859 |
| 3,828,791 | 4,777,948 | 5,089,000 |
| 3,888,117 | 4,792,333 | 5,108,406 |
| 4,066,082 | 4,944,741 | 5,176,700 |
| 4,105,030 | 4,994,079 | 5,190,541 |
| 4,174,715 | 5,030,216 | 5,290,299 |
| 4,201,213 | 5,014,407 | 5,324,518 |
| 4,414,985 | 5,047,046 | SU 1949059 |

None of these devices, however, provide a suitable grasping or holding device having an opposed thumb and an articulated, controllable finger, which operates much like the human hand. Furthermore, none of the known devices provide a means for providing and maintaining an internal space in the human body in which other operations can be performed.

SUMMARY OF THE INVENTION

It is an object of the present invention to provide a surgical instrument which can be provided internally in a human or animal body for grasping and performing operations within the body.

Further, an object of the present invention is to provide a surgical device which can be used to provide and maintain internal cavities in the body in which other operations can be performed.

Yet still a further object of the present invention is to provide a surgical instrument which can provide the means to deliver other medical tools into an area of a human or animal body in which an operation is to be performed. Such tools might comprise, for example and without limitation, scalpels, scissors, cauterizers, fiber optical devices, lasers, drug delivery devices, biopsy devices, etc.

It is yet still a further object of the present invention to provide a surgical instrument which mimics, on a smaller scale, the human hand.

It is thus an object of the present invention to provide a surgical instrument which is versatile, convenient to use and which allows the surgeon to manipulate it at a distance from the operational area in a comfortable manner.

The above and other objects of the invention are achieved by a surgical apparatus comprising a support rod having proximal and distal ends; at least one articulated finger at the distal end of the support rod; a handle at the proximal end of the supported rod, the handle having a finger grip adapted to be actuated by the hand of a user; a connecting member connecting the finger grip and the finger; a thumb being disposed at the distal end opposite the finger; a spring biasing the finger toward a retracted position; the finger being responsive to a tension in the cable exerted by movement of the finger grip whereby the finger moves in a defined manner toward the thumb for grasping an object.

According to another aspect, the invention is a surgical apparatus comprising a support rod having proximal and distal ends; a plurality of articulated fingers at the distal end of the support rod; a handle at the proximal end of the support rod, the handle having a finger grip adapted to be actuated by the hand of a user; at least one cable connecting the finger grip and the fingers; a spring biasing the fingers toward a retracted position; and the fingers being responsive to a tension in the cable exerted by movement of the finger grip whereby the fingers move in a defined manner away from each other to generate a space between the fingers to facilitate a surgical operation.

The invention provides an operating tip which allows a surgeon to manipulate tissue or organs in a manner similar to using one's own hand. The operating tip consists preferably of a plurality of "fingers" which bend at discrete joints to allow grasping objects in a three-dimensional way. Using cables or wires to control the flexing or extension of the fingers, a surgeon can wrap the fingers completely around an object. The flexion of the fingers creates a tissue or organ grasping capability, while the extension of the fingers creates a tissue or organ displacement capability, i.e., allowing the opening up of a space within a body.

In a grasping capacity, an object held within the fingers can be stabilized while a secondary instrument is used to perform a repair task on the object. The secondary surgical instrument could be used to cut, coagulate, dissect, take biopsy samples, suction, irrigate, deliver drug doses or perform any other 10 surgical task on the object. The secondary instrument could be used as a complementary instrument, or as an integral part of the device by being inserted through a hollow shaft or lumen of the device until the distal tip of the secondary instrument is exposed and can be applied to the object held within the fingers of the device. By attaching netting or webbing to the fingers, a glove or basket can be formed to add further grasping control features to the device.

In the displacement capacity, tissue or organs can be displaced to provide better visualization of the surgical site, or to allow better access into the surgical site. Improved visualization or access can be achieved by moving obstructing objects out of the line of sight by inserting the extended fingers (which are close together) into an opening in the surgical site and then flexing the fingers partially (or completely), thus spreading the adjacent tissue or organ(s) away from what would be the "palm" area of the device. By adding webbing or netting to connect the fingers, an umbrella could be formed to better improve visualization.

As the device is to be used internally in a human or animal body, it preferably should be made of biocompatible materials, such as stainless steels, plastics, silicones, etc.

According to yet still another aspect, the inventor comprises surgical apparatus comprising a support rod having proximal and distal ends; a plurality of articulated fingers at the distal end of the support rod; a handle at the proximal end of the support rod, the handle having a finger grip adapted to be actuated by the hand of a user; at least one connecting member connecting 10 the finger grip and the fingers; a spring biasing the fingers toward a retracted position; and the fingers being responsive to a tension in the connecting member exerted by movement of the finger grip whereby the fingers move in a defined manner away from each other against the bias of the spring to allow the fingers to grasp an object therebetween to facilitate a surgical operation.

Other features and advantages of the present invention will become apparent from the following description of the invention which refers to the accompanying drawings.

BRIEF DESCRIPTION OF THE DRAWING(S)

The invention will now be described in greater detail in the following detailed description with reference to the drawings in which:

FIG. 3 is side view of a fingertip of a finger of the surgical device;

FIG. 3A is a left end view of the fingertip of the surgical device;

FIG. 4 is a sectional view along line A—A of FIG. 3A;

FIG. 5 is a right end view of the fingertip shown in FIG. 3;

FIG. 6 is a bottom view of the fingertip shown in FIG. 3;

FIG. 7 is a side view of a finger middle 10 portion of a finger of the surgical device;

FIG. 8 is a top view of the finger middle portion shown in FIG. 7;

FIG. 9 is a partial view of the finger middle portion of FIG. 7;

FIG. 10 is an end view of the left side of the finger middle portion shown in FIG. 9;

FIG. 11 is a top view of the hinge of the right finger of the surgical device shown in FIGS. 1 and 2;

FIG. 12 is a bottom end view of the right hinge shown in FIG. 11;

FIG. 13 is a side view, viewing from the right in FIG. 11, of the right hinge;

FIG. 14 is a perspective view of the right hinge viewed along lines A—A of FIG. 12;

FIG. 15 is an end view of the handle frame of the surgical device;

FIG. 16 is a top view of the handle frame of the surgical device shown in FIG. 15;

FIG. 17 is an end view of the handle frame of the surgical device shown viewed from the bottom of FIG. 16;

FIG. 18 is a top view of the left hinge of the surgical device;

FIG. 19 is an end view of the left hinge of the surgical device shown from the bottom in FIG. 18;

FIG. 20 is a perspective view of the hinge of the left finger of the surgical device viewed along lines A—A of FIG. 19;

FIG. 21 is a side view of the left hinge of the surgical device shown in FIG. 18 viewed along the left side of FIG. 18;

FIG. 22 is a side view of the thumb portion of the surgical device;

FIG. 23 is a side view of the handle frame shown in FIG. 16;

FIG. 24 is a top view of the support rod of the surgical device shown in FIGS. 1 and 2;

FIG. 24A is an end view viewed from the right side of FIG. 24 of the support rod of the surgical device;

FIG. 25 is a side view of the support rod shown in FIG. 24;

FIG. 26 is a sectional along line C—C of FIG. 25;

FIG. 27 is a sectional view along line B—B of FIG. 25;

FIG. 28 is a sectional view along line A—A of FIG. 25;

FIG. 29 is a top view of the handle grip of the surgical device;

FIG. 30 is a top view of one of the two finger grips of the surgical device;

FIG. 31 is an end view of the finger grip of FIG. 30 shown from the bottom of FIG. 30;

FIG. 31A shows in schematic form one arrangement of the control cable for flexing the finger and the biasing return spring;

FIG. 31B shows another arrangement of the control cable and biasing return spring;

FIG. 32 is a pictorial illustration of a modified form of the invention having three fingers which can be used to open up an internal cavity in a body;

FIG. 33 is a schematic view of an opening in a body which can be made by the device shown in FIG. 32;

FIG. 33A is a schematic view of another opening in a body which can be made by the device of FIG. 32;

FIG. 34 shows a different opening which can be made by a modified form of the device shown in FIG. 32, and which has a trapezoidal shape and cross-section;

FIG. 35 shows another opening which can be made by a modified form of the device shown in FIG. 32 and which has a bell shaped opening and cross-section;

FIG. 36 shows the device of FIG. 32 in a schematic cross-sectional view showing three fingers schematically and a central lumen for the provision of other surgical instruments or optical fibers;

FIG. 37 shows a modified form of the device of FIG. 32 having a greater number of fingers, in the case shown, eight fingers;

FIG. 38 shows how a bell-shaped curve and thus a bell shaped body cavity can be provided by the fingers of a modified form of the device shown in FIG. 32;

FIG. 39 shows a cross-section taken along line A—A of FIG. 38;

FIG. 40 shows how the rounded conical-shaped body cavity of FIG. 33A can be provided; and FIG. 41 shows the embodiment of FIG. 32 which is suitable for grasping, a suction tip being shown at the end of a finger in this exemplary embodiment.

DETAILED DESCRIPTION OF THE INVENTION

Figure 1:
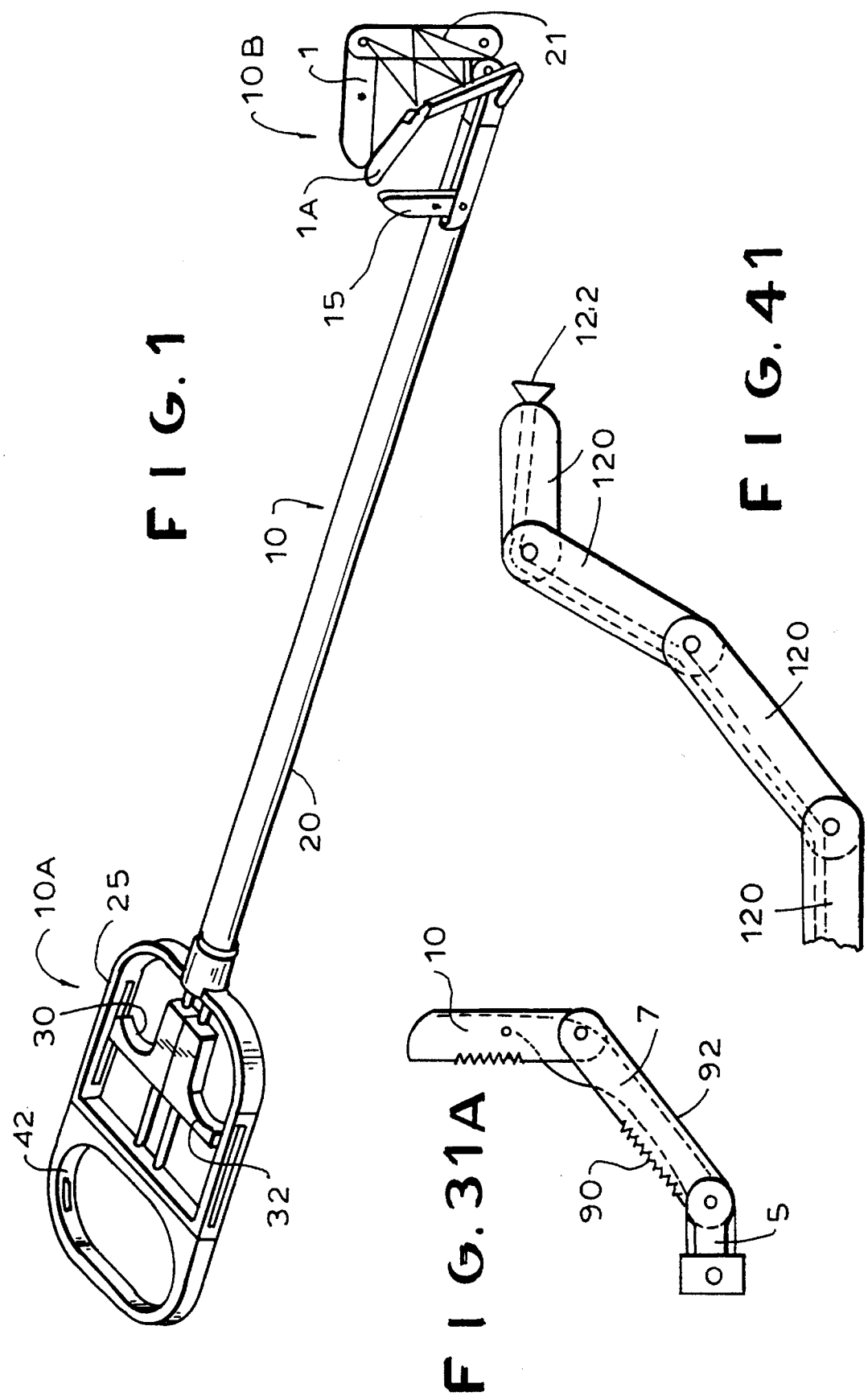
FIG. 1 shows a perspective view of one embodiment of a surgical instrument according to the present invention.

With reference now to the drawings, FIG. 1 shows a perspective view of the surgical device according to the present invention. The surgical device can be called a "surgeon's hand" because it allows a surgeon to manipulate tissue or organs in a manner similar to using one's own hand. The device of the present invention may be applied in the medical/surgical field and is primarily used for the manipulation of tissue and organs in minimally invasive surgery. As described above and below, the device can be used for manipulating tissue and organs to be operated on by another instrument. The device in the modified form shown in FIG.

32 can also be used to provide a displacement function, i.e., to open up a cavity in a body to facilitate another operation by improving visibility and access.

Figure 2:
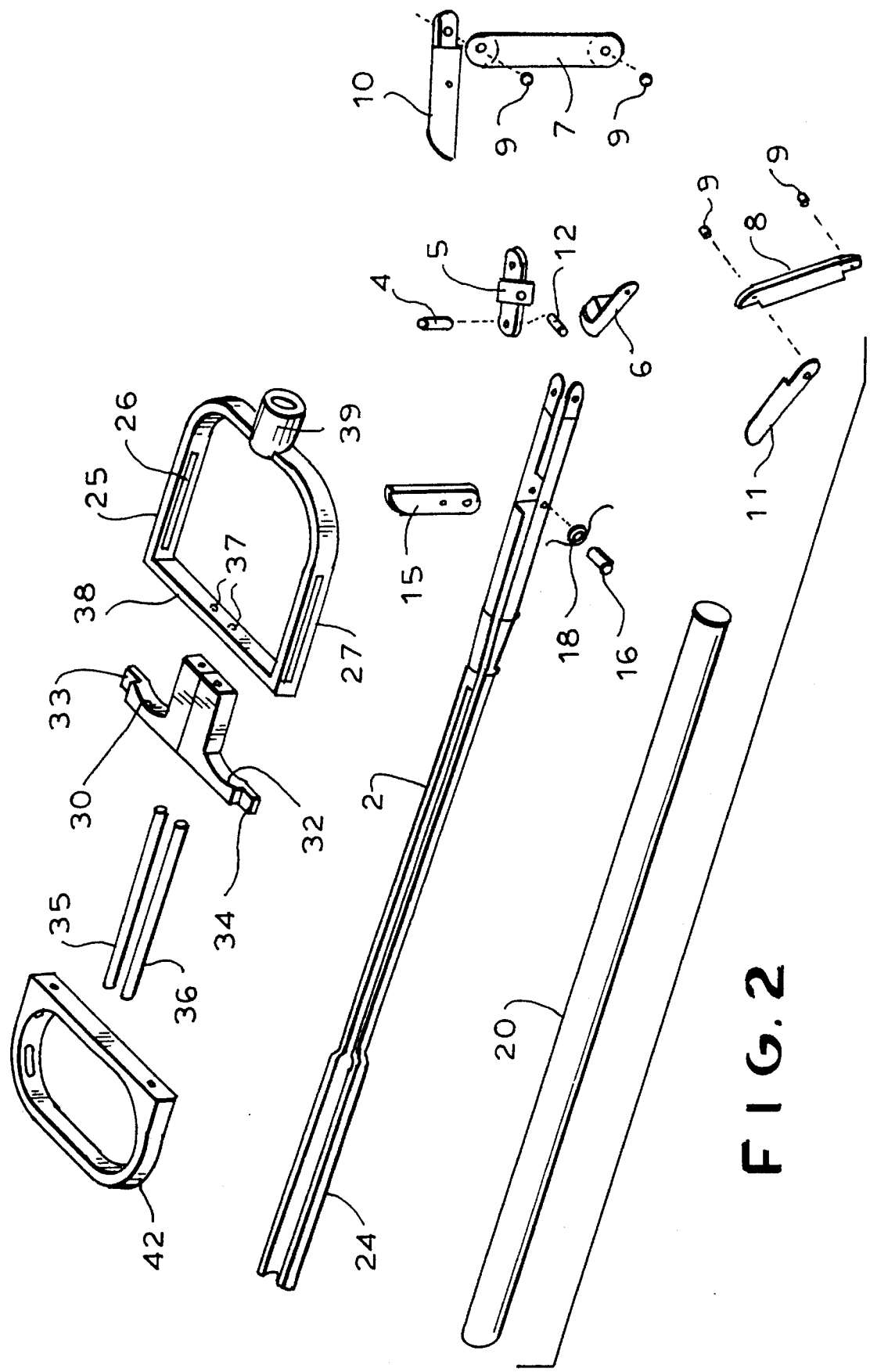
FIG. 2 shows an exploded view of the device of FIG. 1.

Turning now to FIGS. 1 and 2, which show the "surgeon's hand" the device, generally designated 10, comprises a support rod 2, which is suitably shaped with grooves for the provision of cables or wires extending from the handle end 10A to the finger end 10B and which control the manipulation of a plurality of fingers 1 and 1A at the end 10B. Although two fingers are shown, the device can have only one finger or a plurality of fingers greater than two. In the embodiment shown, finger 1 is defined as the left finger and finger 1A the right finger. Each finger comprises a plurality of finger portions, to be described.

At the distal end 10B of the support rod 2, shown to the right in FIG. 2, two hinges 5 and 6 are provided. The hinge 5 of the left finger and the hinge 6 of the right finger are pivotally connected through an opening in a forked end 3 of the support rod 2 by a pivot pin 4. As shown in FIGS. 11–14, which shows the right hinge 6, each hinge includes a first pivot section 6' which receives the common pivot pin 4 and is received in a bore of the forked distal end 3 of the support rod 2. The hinge 6 is then turned at a right angle, as shown, to form a second pivot area 6", which is coupled to a middle finger portion 8. The hinge 6 includes a slot 55 for the control cable as well as a bore 56 for the return spring, to be described later. The hinge also includes a partial bore 6''' which functions as a spring seat receiving a compression spring 12. The left hinge 5 is substantially identical to right hinge 6, except it is a mirror image of the right hinge. It is shown in detail in FIGS. 18–21, but will not be further described. Its pivot areas are designated 5' and 5" and the compression spring seat is 5'''.

Each of the hinges 5 and 6 are connected to a respective finger middle portion 7 and 8, 7 being the left finger middle portion and 8 being the right finger middle portion. The finger middle portions 7 and 8 are connected to the respective hinge portions 5 and 6 via respective pivot pins 9. The pivot pins 9 may be press-fit into the finger middle portions 7 and 8 or welded to the finger middle portions 7 and 8, allowing them to turn freely on the respective hinge portions 5 or 6. Alternatively, the pivot pins 9 can be secured firmly to the respective hinge portions 5 or 6 and allowed to rotate in the finger middle portion 7 or 8.

Left finger middle portion 7 is pivotally connected by another pivot pin 9 to the left finger tip portion 10. Similarly, right finger middle portion 8 is pivotally connected to a right finger tip portion 11 via another pivot pin 9.

Between respective hinges 5 and 6, a compression spring 12 is provided in the seat recesses 6''' and 5''' which forces the two hinges 5 and 6 apart.

In a bore 14 provided at a distance from the distal end of the support rod 2, a thumb 15 is pivotally mounted on a pivot pin 16. A torsion spring 18 is provided to force the thumb into its upright position shown in FIG. 2. A slot 22 is provided in rod 2 for receiving thumb 15 in its retracted position.

An outer sleeve 20 is slidably disposed over the support rod 2. The outer sleeve 20 is provided so that it can be slid up to and against the thumb 8, thereby forcing the thumb against the action of spring 18 into slot 22 provided at the distal end of the support rod 2. Upon further slidable movement of the outer sleeve 20 towards the distal end of the support rod 2, the outer sleeve will contact the two hinges 5 and 6, forcing the hinges towards each other against the action of the compression spring 12. This action will cause the finger portions to move together. Upon even further slidable movement of the outer sleeve 10, the outer sleeve will engage the finger middle portions 7 and 8, causing them to pivot so that they are essentially in line with the support rod 2, i.e., they lie in their retracted position in a straight line defined by the support rod 2. Upon even further slidable movement of the outer sleeve 20, it will contact the finger tips 10 and 11, causing them also to lie in the retracted position defined by the support rod 2. Accordingly, in the retracted position, the outer sleeve substantially encloses the entire finger portions and the thumb, and then the distal end is in a position to be inserted easily internally in a body for a surgical operation.

The support rod 2, shown in more detail in FIGS. 24 and 25, is provided with a plurality of grooves, in this case two, for the slidable movement of wires or cables which are connected to left and right finger grips 30 and 32. The grooves are shown at 22 and 24 in FIG. 24. Suitable wires or cables are disposed in these grooves for manipulating the left and right fingers 1 and 1A and are constrained in position in the grooves by the outer sleeve 20.

The surgical device has a generally open D-shaped handle frame 25 disposed at the proximal end of or spot-welded to the support tube 2, with the attachment or welding being made so as to avoid welding near the grooves 22 and 24. The handle frame 25 includes grooves 26 and 27 on opposite sides thereof which receive tips 33 and 34 of respective left and right finger grips 30 and 32 in slidable relationship. The finger grips 30 and 32 are also slidably supported on respective support rods 35 and 36, which are received in holes 37 in an end portion 38 of the D-shaped handle frame 25 and also in holes provided in the attachment portion 39 of the handle frame 25. Further details of the handle frame 25 are shown in FIGS. 15, 16 and 17. The support rods 35 and 36 are secured in holes 40 provided in the attachment portion 39 of the handle frame 25, which attachment portion is itself preferably welded to the D-shaped portion of the handle frame.

At the proximal end 10B of the device 10, a handle grip 42 is provided which is secured to the handle frame 25 via suitable fasteners such as screws received in openings 44 in the end portion 38 of the handle frame 25. Handle grip 42 is adapted for insertion of the user's hand therethrough, with the fingers being received in the finger grips.

Suitable wires or cables, not shown in FIG. 2, are secured to the left and right finger grips 30 and 32 which are slidably mounted on the respective support rods 35 and 36. Left finger grip 30 is provided with a wire or cable which extends through the securement portion 39 of the handle frame, through the groove 22 longitudinally down the support rod 2 and inside the outer sleeve 10, and then along the distal end of the support rod 2 in a continuation of the groove 22 as shown in FIG. 28, which is taken along the line A—A of FIG. 25. The wire or cable is provided through a groove 45 provided in the left hinge, as shown most clearly in FIGS. 18 and 19. The wire or cable extends through the longitudinal groove 45 and then along a groove 47 provided in the left finger middle portion 7, shown in greater detail in FIGS. 7 through 10. The wire or cable is unrestrained where the cable extends over the joint between the hinge 5 and the finger middle portion 7 and is restrained in the groove 47, i.e., kept from moving out of the groove, by suitably closing off the top of the groove 47. However, the cable is not fixed in the groove so that it is able to move slidably within the groove 47.

At the distal end of the finger middle portion 7, the cable again is unrestrained as it passes over the joint between finger middle portion 7 and the left fingertip portion 10, shown most clearly in FIGS. 3, 3A, 4, 5 and 6. The cable is secured via a suitable set screw 50 in the fingertip portion 10, and preferably at an angle of 15° with respect to the finger tip surface, as shown in FIG. 4. In this way, when the finger grip 30 is moved slidably upon its support rod 35 toward the handle grip 42, with the outer sleeve 20 moved to expose the finger and thumb elements, depending upon the pressure applied to the grip portion 30, the finger 1 portion comprising the fingertip 10 and finger middle portion 7 will move in a curling manner to enable grasping of an object against the thumb 15.

In like fashion, another cable is provided in groove 24 extending from the finger grip portion 32, and thence through a groove 55 in the right hinge 6 over the joint between the right hinge 6, and the finger middle portion 8, passing restrained in a groove (like 47) in the right finger middle portion 8, unrestrained over the joint between the right finger portion 8 and the right fingertip portion 11 and secured, as shown in FIG. 3 by a set screw (like 50) in the right finger portion 11.

The right tip finger portion 11 and the finger middle portion 8 are essentially the same as the corresponding left finger portions shown in FIGS. 3 through 10, although they are a mirror image of the left finger portions shown in those figures.

In order to provide a suitable return spring action so that the fingers 1 and 1A and finger grips 30 and 32 return to a retracted position, although not necessarily the completely retracted position of the distal fingers obtained when the outer sleeve 10 is slidably disposed over the finger portions, another lower set of openings or grooves is provided in the hinges 5 and 6, finger middle portions 7 and 8 and fingertip portions 10 and 11. In the left hinge 5, a suitable opening 60 is provided, into which a longitudinally extending flexible spring element is provided. The spring element, which may be a spring wire, extends and is secured in the opening 60 in the hinge 5, extends over the joint between the hinge 5 and the finger middle portion 7, through a groove 57 provided in the finger middle portion 7 and then over the joint between the finger middle portion 7 and the fingertip portion 10. The longitudinally extending spring element is then received in a bore 65 provided in the fingertip portion 10.

Accordingly, when the finger is curled by tension in the cable actuated by the action of the finger grip 30, it curls against the action of the longitudinally extending spring. When the surgeon's hand pressure is removed from the finger grip 30, the curled finger uncurls against the action of the longitudinally extending wire spring, which seeks to straighten. The wire spring is not secured at least at one end to the hinge 5 or finger tip 10, as it must be free to slide in at least two of the three finger portions.

Alternatively, a longitudinally extending coil spring can be provided instead of a wire spring. Since the coil spring can stretch, it is preferably secured at one end to the hinge 5 and at the other end to the finger tip 10.

In similar fashion, a wire spring is also provided in the right finger elements comprising the right hinge 6, finger middle portion 8 and right fingertip portion 11. Suitable openings 56, 57 are provided in each of these finger portions for securing the wire spring therein which tends to bias the finger to its open position when the pressure on the finger grip 32 is removed.

As shown most clearly in FIG. 22, the fingertip portions 10 and 11 include suitable serrations 80 to enable gripping. Finger middle portions 7 and 8 are also preferably provided with suitable serrations 82, as shown most clearly in FIGS. 7 and 8.

FIG. 31A schematically shows the routing of the cable, identified with 90, and the spring wire or coil spring, identified with 92.

FIG. 31A shows the left finger comprising the left hinge 5, left finger middle portion 7 and left fingertip portion 10. The right finger is a mirror image of the left finger. The cable connected to the left finger grip 30 and extending through the rod 2 is shown at 90. The flexible spring which allows the finger to move from its curled position to an uncurled position is shown at 92.

FIG. 31B shows an alternative embodiment in which cable 90 is restrained in tubes or sheaths 91. The tubes 91 are fastened to the finger elements 5, 7 and 8 of the left finger (and similarly for the right finger). The cable is free to slide in the tubes 91, but is restrained against normal forces. The cable can bend at the joints without restraint of the tubes 91, as shown. Similarly, spring element 92 is restrained against normal forces in tubes 93 secured to the finger elements, and is free to bend at the joints, unrestrained by the tubes.

In operation, the surgical device is inserted through a body opening with the outer sleeve 10 extended fully to cover the finger portions and the thumb. Once inside the body, the outer sleeve 10 may be moved toward the proximal end, i.e., towards the securement portion 39 of the handle frame 25. This will allow the action of the spring 12 to force the two fingers away from each other, and at the same time, allow the spring 92 in the grooves of the finger portions to allow the fingers to curl to a limited extent. The surgeon can then manipulate the finger grips 30 and 32 to control the amount of curl and to grab a body part between the fingers and the opposed thumb 15.

In a preferred embodiment, support rod 2 is provided with a central bore (not shown), through which another cable or fiber is disposed. The fiber can be an optical fiber for providing illumination or a laser beam to the surgical site, or alternatively, for providing a signal for a display monitor to show the ongoing surgical procedure. Alternatively, the fiber or cable can be used to control other surgical devices at the surgical site, or can be a tube to deliver a dose of a drug, or an electrical cable for delivering an electrical current.

Additionally, to improve holding capacity, wire, netting or webbing can be provided between the fingers 1 and 1A. This is shown illustratively by the lines 21 in FIG. 1. Preferably the netting comprises a stretchable, elastic material.

In an alternative embodiment of the present invention, an opposed thumb need not be provided. Instead, only a plurality of fingers are provided. For example, three fingers could be provided as shown in the embodiment of FIG. 32. Although three fingers 101 are shown in FIG. 32, as few as two fingers could be provided. Further, a larger number of fingers could be provided. In FIG. 36, a cross-section is shown in which three fingers are provided with a central lumen 100 being provided so that other surgical instruments or filaments can be provided to the operating site, as previously described and as will be described below. FIG. 37 shows an embodiment in which eight fingers 101 are provided.

The embodiment of FIG. 32 is useful in situations where it is desired to provide an interior space or cavity within the body in which an operation is to be performed. For example, it may be necessary to move organs so as to define an internal space for a surgical procedure or other operation. The device of FIG. 32 is inserted into the body in the retracted position, with the slidable sleeve 20 (not shown in FIG. 32) being moved so as to cover the fingers. The sleeve is then moved to expose the fingers, and the finger grips, like the finger grips 30 and 32 shown in the embodiment of FIGS. 1 and 2, are suitably manipulated to open up the interior space. Suitable wires or netting 110 can be provided between the fingertips and also between or around other intermediate portions of the fingers so as to operate as an umbrella or shield to prevent internal organs from entering into the opened-up space 112. This netting, wires or webbing preferably is a stretchable elastic material, and may take the shape of a sock-like member, enclosing the space created by the device (except at the insertion end) and keeping bodily organs from entering the space. As shown in FIG. 32, the device may open up an essentially conical space within the body, i.e, the space generated by revolving a triangle about 360°. Alternatively, the fingers may open up so as to form a generally bell-shaped space, as shown schematically in FIG. 35. FIG. 34 shows another possible interior space generated by the provision of a modified device as shown in FIG. 32 in which the interior space approximates a trapezoid in cross-section, forming a frusto-conical volume. Alternatively, the space may be substantially cylindrical (rectangular in cross section).

FIGS. 33 and 33A show the triangular or conical shape provided by the embodiment of FIG. 32.

In order to change the shape of the volume described by the fingers of the device shown in FIG. 32, it is merely necessary to shift the control cables from one side to the other side of the jointed finger assembly and provide suitable stops, as necessary, at the joints to limit movement as desired. As shown in FIG. 38, for a finger assembly comprising four interconnected segments and intended to generate a bell-shaped figure as shown in FIG. 35 and described by the line 124, each finger is provided with a control cable 120 which is routed along the finger segments as shown in FIG. 38. Thus, at the first and second finger segments 130 and 131, the control cable 120 is routed along the top surface as shown. In the third finger segment 132, the control cable is routed through an opening to the other side of the finger segment where it is finally attached to the fingertip segment 133 at the point 135. The longitudinally-extending retracting spring 122 is provided along the bottom edge of the finger segments 130 and 131, and, prior to the joint between the finger segments 132 and 133 extending from the bottom edge to the top edge, it is then terminated in a longitudinally-extending bore in the fingertip portion 133. As those of skill in the art will appreciate, the single wire or coil spring 134 can be replaced by a plurality of springs, each disposed at a respective joint. This is true also of the embodiment of FIG. 1.

As those of skill in the art will appreciate, when the control cable 120 is flexed, because of the way the cable is routed through the various finger portions, the fingers will flex so as to form a contour along the line indicated by line 124. If a suitable number of fingers is provided, they will generated the bell-shaped curve shown in FIG. 135 and defined by the line 124.

FIG. 40 shows another embodiment, which is essentially the same as the embodiment shown in FIG. 32, and describing an essentially rounded conical-shape as shown in FIG. 33A. In this embodiment, the control cable 120 is provided only along the top edge of each of the fingers 130, 131, 132 and terminating in fingertip 133. The longitudinally-extending retracting spring 122 is provided along the bottom edge, terminating in the longitudinally-extending bore in the fingertip 133. As will be appreciated by those of skill in the art, the longitudinally-extending spring 122 is slidable in at least three of the respective finger portions 130 through 133. At its terminus in at least one of the fingertip portion 133 and proximal portion 130, which may be a hinge portion, it is not fixedly secured to the respective portion, but rather allowed to slide freely.

In use, once the device of FIGS. 32 through FIG. 40 is inserted into the body in the retracted position, the outer sleeve 20 is moved toward the proximal end, thus allowing the fingers to curl away from each other. By suitable operation of finger grips, not shown, but like finger grips 30 and 32 of the embodiment of FIG. 1, the fingers can be moved away from each other to describe an opening in the body. Separate finger grips like 30 and 32 can be provided for each finger 101, or alternatively, a single finger grip operating all fingers 101 in unison can be arranged. In the latter case, one return spring element may be provided or a separate spring element can be provided for each finger. The opening that is described depends upon the routing of the control cables 120 and the springs 122 as well as the provision of any necessary limit stops at the joints, but these openings can define many shapes, as shown by FIGS. 33, 33A, 34 and 35, for example.

Once the cavity has been provided in the body, other devices, which are extendible through the central lumen 100, can be inserted through the central lumen 100 into the space, for performance of a further operation. For example, surgical scalpels, scissors, cauterizers, lasers, drug delivery devices, optical fibers, irrigation/suction devices, biopsy devices, etc., can be provided through the central lumen 100. For example, a fiber optic could be provided to illuminate the space while other instruments are performing another function. A signal can also be provided back to a control console where the image of the surgical procedure can be viewed on a CRT monitor. Thus, the surgeon can view the operation occurring within the cavity 112 created by the displaced fingers of the surgical device. Of course, other surgical instruments can be provided to the operating site by other means, known to those of skill in the art, i.e., directly through the opening in the body in the same manner as the tool of the invention is inserted into the body.

It may also be possible to provide other return spring elements than those shown in the drawings. For example, in the case where a single return spring is provided, it may not be necessary to mount the spring at the fingers, but instead at some other place, e.g., near the finger grip, in which case the spring action will be applied to the fingers through the control cable or cables. Similarly, such a mounting of the return spring or springs can be employed in the embodiment of FIG. 1. For example, a separate return spring could be used at each finger grip, with the spring action then being applied through the respective control cable.

The device of FIG. 32 can also be used to grasp a body part, in addition to opening up a cavity in the body. This allows a surgeon to stabilize the body part for another procedure. The device performing the other procedure may be provided to the surgical site through the central lumen 100 or by other means. The fingers of the device can also be provided with grasping members, i.e., serrations, hooked ends or suction tips to facilitate stabilizing and holding irregular and/or soft body parts. The vacuum for the suction tips can be provided by tubes disposed adjacent each finger or threaded through central openings in the finger sections, as shown by conduits 120 in FIG. 41. A suction tip is shown at 122. The tubes can be made suitably flexible so they bend at the joints. It should also be clear that other grasping devices, e.g., suction tips, can be provided at the finger and thumb tips of the embodiment of FIG. 1.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. Surgical apparatus comprising:
   a support rod having proximal and distal ends;
   a plurality of articulated fingers at the distal end of the support rod;
   a handle at the proximal end of the support rod, the handle having a finger grip adapted to be actuated by the hand of a user;
   a connecting member connecting the finger grip and the articulated fingers;
   a thumb being disposed at the distal end opposite the fingers;
   a spring biasing the fingers toward a retracted position;
   a spring element disposed between adjacent fingers for biasing said fingers away from each other; and
   the fingers being responsive to a tension in the connecting member exerted by movement of the finger grip whereby the fingers move in a defined manner toward the thumb for grasping an object.

2. The surgical apparatus recited in claim 1, wherein each finger comprises a plurality of sections connected by pivot joints, the connecting member being routed such that it is restrained against normal forces adjacent the finger sections and passing unrestrained against normal forces adjacent the joints, the connecting member being secured at a distalmost one of the finger sections.

3. The surgical apparatus recited in claim 2, wherein the spring comprises a longitudinally extending wire or coil spring extending along the finger sections, the spring being restrained against normal forces at the finger sections and passing unrestrained against normal forces at the joints between the finger sections.

4. The surgical apparatus recited in claim 3, wherein the longitudinally extending spring is restrained in longitudinally extending bores in the finger sections, but is permitted to slide in at least some of said bores.

5. The surgical apparatus recited in claim 3, wherein the connecting member and longitudinally extending spring are disposed in sheaths extending along and attached to the finger sections.

6. The surgical apparatus recited in claim 5, wherein the connecting member and spring are exposed adjacent the joints between finger sections.

7. The surgical apparatus recited in claim 2, wherein the finger sections have grasping surfaces thereon to facilitate gripping.

8. The surgical apparatus recited in claim 2, wherein the connecting member is restrained in slots in the finger sections, but is permitted to slide in at least some of said slots.

9. The surgical apparatus recited in claim 2, wherein each finger comprises at least three sections, with one of the sections comprising a hinge member where each finger is pivotally coupled to the support rod.

10. The surgical apparatus recited in claim 1, wherein the finger grip is slidably disposed on a support element disposed in a generally open handle adapted for receiving the fingers of a user.

11. The surgical apparatus recited in claim 1, further wherein the support rod has a bore provided for routing a filament to a surgical site for the performance of an additional function.

12. The surgical apparatus recited in claim 11, further comprising a filament in the bore of the support rod and wherein the filament comprises an optical fiber for one of illumination, providing a laser beam to the surgical site or providing a viewing signal back to a display monitor.

13. The surgical apparatus recited in claim 11, further comprising a filament in the bore of the support rod and wherein the filament is provided for controlling a surgical instrument.

14. The surgical apparatus recited in claim 1, wherein the connecting member comprises a wire or cable.

15. Surgical apparatus comprising:
    a support rod having proximal and distal ends;
    at least one articulated finger at the distal end of the support rod;
    a handle at the proximal end of the support rod, the handle having a finger grip adapted to be actuated by the hand of a user;
    a connecting member connecting the finger grip and the articulated finger;
    a thumb being disposed at the distal end opposite the finger;
    a spring biasing the finger toward a retracted position;
    the finger being responsive to a tension in the connecting member exerted by movement of the finger grip whereby the finger moves in a defined manner toward the thumb for grasping an object; and
    further comprising a sleeve extending over said support rod, the sleeve being slidable over the support rod and wherein said thumb and articulated finger are pivotally mounted on the support rod, the sleeve being slidable so as to force said thumb and said articulated finger into a fully open retracted position wherein the thumb and finger extend longitudinally in line with said support rod, the sleeve being slidable to cover said thumb and finger in the retracted position to facilitate entry of the distal end into an opening in a body for a surgical procedure.

16. The surgical apparatus recited in claim 15, wherein the connecting member is routed in a groove disposed in the support rod, the connecting member being constrained in the groove by the sleeve.

17. The surgical apparatus recited in claim 15, wherein the thumb is pivotable into a slot in the support rod when the sleeve forces the thumb into the retracted position.

18. Surgical apparatus comprising:
    a support rod having proximal and distal ends;
    a plurality of articulated fingers at the distal end of the support rod;
    a handle at the proximal end of the support rod, the handle having a finger grip adapted to be actuated by the hand of a user;
    a connecting member connecting the finger grip and the articulated fingers;
    a thumb being disposed at the distal end opposite the fingers;
    a spring biasing the fingers toward a retracted position;
    the fingers being responsive to a tension in the connecting member exerted by movement of the finger grip whereby the fingers move in a defined manner toward the thumb for grasping an object; and
    further comprising netting extending between fingers for facilitating holding objects.

19. Surgical apparatus comprising:

a support rod having proximal and distal ends;

a plurality of articulated fingers at the distal end of the support rod;

a handle at the proximal end of the support rod, the handle having a finger grip adapted to be actuated by the hand of a user;

at least one connecting member connecting the finger grip and the fingers;

a spring biasing the fingers toward a retracted position;

a spring element disposed between adjacent fingers for biasing said fingers away from each other; and the fingers being responsive to a tension in the connecting member exerted by movement of the finger grip whereby the fingers move in a defined manner away from each other to generate a space between the fingers to facilitate a surgical operation.

20. The surgical apparatus recited in claim 19, wherein each finger comprises a plurality of sections connected by pivot joints, the connecting member being routed such that it is restrained against normal forces adjacent the finger sections and passing unrestrained against normal forces adjacent the joints, the connecting member being secured at a distalmost one of the finger sections.

21. The surgical apparatus recited in claim 20, wherein the spring comprises a longitudinally extending wire or coil spring extending along the finger sections, the spring being restrained against normal forces by the finger sections and passing unrestrained against normal forces at the joints between the finger sections.

22. The surgical apparatus recited in claim 21, wherein the longitudinally extending spring is restrained in longitudinally extending bores in the finger sections, but is permitted to slide in at least some of said bores.

23. The surgical apparatus recited in claim 21, wherein the connecting member and longitudinally extending spring are disposed in sheaths extending along and attached to the finger sections.

24. The surgical apparatus recited in claim 23, wherein the connecting member and spring are exposed adjacent joints between finger sections.

25. The surgical apparatus recited in claim 20, wherein the connecting member is restrained in slots in the finger sections but is permitted to slide in at least some of said slots.

26. The surgical apparatus recited in claim 20, wherein each finger comprises at least three sections, with one of the sections comprising a hinge member where the finger is pivotally coupled to the support rod.

27. The surgical apparatus recited in claim 9, wherein the finger grip is slidably disposed on a support element in a generally open handle adapted for receiving the fingers of a user.

28. The surgical apparatus recited in claim 27, wherein the finger grip comprises a plurality of finger grip portions, one for each finger.

29. The surgical apparatus recited in claim 28, wherein the connecting member comprises a separate connecting member for each finger.

30. The surgical apparatus recited in claim 19, further wherein the support rod has a bore provided for routing a filament to a surgical site for the performance of an additional function.

31. The surgical apparatus recited in claim 30, further comprising a filament in the bore of the support rod and wherein the filament comprises an optical fiber for one of illumination, providing a laser beam to the surgical site or providing a viewing signal back to a display monitor.

32. The surgical apparatus recited in claim 30, further comprising a filament in the bore of the support rod and wherein the filament is provided for controlling a surgical instrument.

33. The surgical apparatus recited in claim 19, wherein the fingers can be moved by the finger grip to generate a space between the fingers defining one of a cone, bell-shape, frusto conical shape and cylinder.

34. The surgical apparatus recited in claim 19, wherein the connecting member comprises a wire or cable.

35. The surgical apparatus recited in claim 19, wherein the fingers are also adapted to grasp a body part for stabilizing the body part for a surgical procedure.

36. The surgical apparatus recited in claim 35, wherein the fingers are provided with suction tips for facilitating grasping of a body part.

37. Surgical apparatus comprising:

a support rod having proximal and distal ends;

a plurality of articulated fingers at the distal end of the support rod;

a handle at the proximal end of the support rod, the handle having a finger grip adapted to be actuated by the hand of a user;

at least one connecting member connecting the finger grip and the fingers;

a spring biasing the fingers toward a retracted position;

the fingers being responsive to a tension in the connecting member exerted by movement of the finger grip whereby the fingers move in a defined manner away from each other to generate a space between the fingers to facilitate a surgical operation; and further comprising a sleeve extending over said support rod, the sleeve being slidable over the support rod and wherein said fingers are pivotally mounted in the support rod, the sleeve being slidable so as to force said fingers into a fully open retracted position wherein the fingers extend longitudinally in line with said support rod, the sleeve being slidable to cover said fingers in the retracted position to facilitate entry of the distal end into an opening in a body for a surgical procedure.

38. The surgical apparatus recited in claim 37, wherein the connecting member is routed in a groove disposed in the support rod, the connecting member being constrained in the groove by the sleeve.

39. Surgical apparatus comprising:

a support rod having proximal and distal ends;

a plurality of articulated fingers at the distal end of the support rod;

a handle at the proximal end of the support rod, the handle having a finger grip adapted to be actuated by the hand of a user;

at least one connecting member connecting the finger grip and the fingers;

a spring biasing the fingers toward a retracted position;

the fingers being responsive to a tension in the connecting member exerted by movement of the finger grip whereby the fingers move in a defined manner away from each other to generate a space between the fingers to facilitate a surgical operation; and further comprising wires or netting extending between adjacent ones of said fingers for facilitating maintaining said space between the fingers and preventing entry of internal body parts into said space.

40. Surgical apparatus comprising:

a support rod having proximal and distal ends;

a plurality of articulated fingers at the distal end of the support rod;

a handle at the proximal end of the support rod, the handle having a finger grip adapted to be actuated by the hand of a user;

at least one connecting member connecting the finger grip and the fingers;

a spring biasing the fingers toward a retracted position;

the fingers being responsive to a tension in the connecting member exerted by movement of the finger grip whereby the fingers move in a defined manner against the bias of the spring to allow the fingers to grasp an object therebetween to facilitate a surgical operation; and wires or netting extending between adjacent fingers for facilitating maintaining a space between the fingers and preventing entry of internal body parts into the space.

41. The surgical apparatus recited in claim 40, wherein the fingers are provided with suction tips for facilitating grasping of an object.

42. Surgical apparatus comprising:

a support rod having proximal and distal ends;

a plurality of flexible fingers at the distal end of the support rod;

a handle at the proximal end of the support rod, the handle having a finger grip adapted to be actuated by the hand of a user;

a connecting member connecting the finger grip and the flexible fingers;

a thumb being disposed at the distal end opposite the fingers;

a spring element disposed between adjacent fingers for biasing said fingers away from each other; and the fingers being responsive to a tension in the connecting member exerted by movement of the finger grip whereby the fingers move in a defined manner toward the thumb for grasping an object.

43. The surgical apparatus recited in claim 42, wherein the flexible finger comprises articulated fingers.

44. The surgical apparatus recited in claim 42, further comprises a spring biasing each finger toward a retracted position.

45. The surgical apparatus recited in claim 42, wherein the finger grip is slidably disposed on a support element disposed in a generally open handle adapted for receiving the fingers of a user.

46. The surgical apparatus recited in claim 42, wherein the connecting member is disposed in a bore in each flexible finger.

47. The surgical apparatus recited in claim 42, further wherein the support rod has a bore provided for routing a filament to a surgical site for the performance of an additional function.

48. The surgical apparatus recited in claim 47, further comprising a filament in the bore of the support rod and wherein the filament comprises an optical fiber for one of illumination, providing a laser beam to the surgical site or providing a viewing signal back to a display monitor.

49. The surgical apparatus recited in claim 47, further comprising a filament in the bore of the support rod and wherein the filament is provided for controlling a surgical instrument.

50. The surgical apparatus recited in claim 42, wherein the connecting member comprises a wire or cable.

51. Surgical apparatus comprising:

a support rod having proximal and distal ends;

at least one flexible finger at the distal end of the support rod;

a handle at the proximal end of the support rod, the handle having a finger grip adapted to be actuated by the hand of a user;

a connecting member connecting the finger grip and the flexible finger;

a thumb being disposed at the distal end opposite the finger;

the finger being responsive to a tension in the connecting member exerted by movement of the finger grip whereby the finger moves in a defined manner toward the thumb for grasping an object; and further comprising a sleeve extending over said support rod, the sleeve being slidable over the support rod and wherein said thumb and flexible finger are pivotally mounted on the support rod, the sleeve being slidable so as to force said thumb and said flexible finger into a fully open retracted position wherein the thumb and finger extend longitudinally in line with said support rod, the sleeve being slidable to cover said thumb and finger in the retracted position to facilitate entry of the distal end into an opening in a body for a surgical procedure.

52. The surgical apparatus recited in claim 51, wherein the connecting member is routed in a groove disposed in the support rod, the connecting member being constrained in the groove by the sleeve.

53. The surgical apparatus recited in claim 51, wherein the thumb is pivotable into a recess in the support rod when the sleeve forces the thumb into the retracted position.

54. Surgical apparatus comprising:

a support rod having proximal and distal ends;

a plurality of flexible fingers at the distal end of the support rod;

a handle at the proximal end of the support rod, the handle having a finger grip adapted to be actuated by the hand of a user;

a connecting member connecting the finger grip and the flexible fingers;

a thumb being disposed at the distal end opposite the fingers;

the fingers being responsive to a tension in the connecting member exerted by movement of the finger grip whereby the fingers move in a defined manner toward the thumb for grasping an object; and further comprising netting extending between fingers for facilitating holding objects.

55. Surgical apparatus comprising:

a support rod having proximal and distal ends;

a plurality of flexible fingers at the distal end of the support rod;

a handle at the proximal end of the support rod, the handle having a finger grip adapted to be actuated by the hand of a user;

at least one connecting member connecting the finger grip and the fingers;

a spring element disposed between adjacent fingers for biasing said fingers away from each other; and the fingers being responsive to a tension in the connecting member exerted by movement of the finger grip whereby the fingers move in a defined manner away from each other to generate a space between the fingers to facilitate a surgical operation.

56. The surgical apparatus recited in claim 55, wherein the flexible fingers each comprise articulated fingers.

57. The surgical apparatus recited in claim 55, further comprising a spring biasing the fingers toward a retracted position.

58. The surgical apparatus recited in claim 55, wherein the finger grip is slidably disposed on a support element in a generally open handle adapted for receiving the fingers of a user.

59. The surgical apparatus recited in claim 58, wherein the finger grip comprises a plurality of finger grip portions, one for each finger.

60. The surgical apparatus recited in claim 55, wherein the connecting member is routed in a groove disposed in the support rod, the connecting member being constrained in the groove by the sleeve.

61. The surgical apparatus recited in claim 60, wherein the connecting member comprises a separate connecting member for each finger.

62. The surgical apparatus recited in claim 55, wherein the connecting member comprising a plurality of connecting members slidably restrained in bores in each finger.

63. The surgical apparatus recited in claim 55, further wherein the support rod has a bore provided for routing a filament to a surgical site for the performance of an additional function.

64. The surgical apparatus recited in claim 63, further comprising a filament in the bore of the support rod and wherein the filament comprises an optical fiber for one of illumination, providing a laser beam to the surgical site or providing a viewing signal back to a display monitor.

65. The surgical apparatus recited in claim 63, further comprising a filament in the bore of the support rod and wherein the filament is provided for controlling a surgical instrument.

66. The surgical apparatus recited in claim 55, wherein the fingers can be moved by the finger grip to generate a space between the fingers defining one of a cone, bell-shape, frusto conical shape and cylinder.

67. The surgical apparatus recited in claim 55, wherein the connecting member comprises a wire or cable.

68. The surgical apparatus recited in claim 55, wherein the fingers are also adapted to grasp a body part for stabilizing the body part for a surgical procedure.

69. The surgical apparatus recited in claim 68, wherein the fingers are provided with suction tips for facilitating grasping of a body part.

70. Surgical apparatus comprising:

a support rod having proximal and distal ends;

a plurality of flexible fingers at the distal end of the support rod;

a handle at the proximal end of the support rod, the handle having a finger grip adapted to be actuated by the hand of a user;

at least one connecting member connecting the finger grip and the fingers;

the fingers being responsive to a tension in the connecting member exerted by movement of the finger grip whereby the fingers move in a defined manner away from each other to generate a space between the fingers to facilitate a surgical operation; and further comprising a sleeve extending over said support rod, the sleeve being slidable over the support rod and wherein said flexible fingers are pivotally mounted in the support rod, the sleeve being slidable so as to force said flexible fingers into a fully open retracted position wherein the fingers extend longitudinally in line with said support rod, the sleeve being slidable to cover said fingers in the retracted position to facilitate entry of the distal end into an opening in a body for a surgical procedure.

71. Surgical apparatus comprising:

a support rod having proximal and distal ends;

a plurality of flexible fingers at the distal end of the support rod;

a handle at the proximal end of the support rod, the handle having a finger grip adapted to be actuated by the hand of a user;

at least one connecting member connecting the finger grip and the fingers;

the fingers being responsive to a tension in the connecting member exerted by movement of the finger grip whereby the fingers move in a defined manner away from each other to generate a space between the fingers to facilitate a surgical operation; and further comprising wires or netting extending between adjacent ones of said fingers for facilitating maintaining said space between the fingers and preventing entry of internal body parts into said space.

72. Surgical apparatus comprising:

a support rod having proximal and distal ends;

a plurality of flexible fingers at the distal end of the support rod;

a handle at the proximal end of the support rod, the handle having a finger grip adapted to be actuated by the hand of a user;

at least one connecting member connecting the finger grip and the fingers;

the fingers being responsive to a tension in the connecting member exerted by movement of the finger grip whereby the fingers move in a defined manner to allow the fingers to grasp an object therebetween to facilitate a surgical operation; and wires or netting extending between adjacent fingers for facilitating maintaining a space between the fingers and preventing entry of internal body parts into the space.

73. The surgical apparatus recited in claim 72, wherein the fingers are provided with suction tips for facilitating grasping of an object.

\* \* \* \* \*